United States Patent [19]

Hughett

[11] 4,350,605
[45] Sep. 21, 1982

[54] WATER-IN-OIL EMULSIONS
[75] Inventor: Paul D. Hughett, Marietta, Ga.
[73] Assignee: Peterson/Puritan, Inc., Danville, Ill.
[21] Appl. No.: 854,062
[22] Filed: Nov. 22, 1977
[51] Int. Cl.³ .............................................. C09K 3/30
[52] U.S. Cl. .................................. 252/305; 252/309;
424/45; 424/46; 424/47; 424/68; 424/357
[58] Field of Search ..................... 424/47, 45, 46, 68;
253/305, 309

[56] References Cited

U.S. PATENT DOCUMENTS

| | | |
|---|---|---|
| 3,137,416 | 6/1964 | Shepherd et al. ............... 424/47 X |
| 3,159,535 | 12/1964 | Sesso et al. ........................ 424/47 |
| 3,509,253 | 4/1970 | Babbin ............................... 424/47 |
| 3,721,693 | 3/1973 | Fein et al. .......................... 424/68 |
| 3,792,068 | 2/1974 | Luedders et al. ............... 424/47 UX |
| 3,798,317 | 3/1974 | Gorum ............................... 424/47 |
| 3,998,788 | 12/1976 | Rubino ............................... 424/68 |

FOREIGN PATENT DOCUMENTS

| | | |
|---|---|---|
| 864527 | 2/1971 | Canada ............................... 424/47 |
| 2442314 | 3/1975 | Fed. Rep. of Germany ........ 424/47 |
| 1381352 | 11/1964 | France ............................... 424/45 |
| 46-28440 | 8/1971 | Japan ................................. 424/47 |
| 48-11024 | 4/1973 | Japan ................................. 424/45 |
| 1161484 | 8/1969 | United Kingdom ................ 424/45 |

OTHER PUBLICATIONS

Soap/Cosm./Chem. Specialties, 10/1976, p. 65.
Soap/Cosm./Chem. Specialties, 01/1977, p. 61.
NL Industries, Chemical for Cosmetics.
Bentone Gel IPM Gelling & Suspending Agent for Cosmetics, NL Industries, 2 pp.
Data Sheet C-3 Toxicity Tests (NL Industries), 2 pp.
Dry Spray Aerosol Antiperspirant, DS-106, 2 pp. (NL Industries).
Roll-On Antiperspirant, DS-106, (NL Indust.) 2 pp.
Antiperspirant Stick, DS-116, (1 p) (NL Industries).
Body Friction Cologne Spray, DS-128 (NL Industries) (1 p).
Du Pont de Nemours & Co., 1956, Aerosol E-Mulsions with "Freon" Propellents.

Primary Examiner—Dale R. Ore

[57] ABSTRACT

Water-in-oil emulsions of improved stability are prepared by using an emulsifying composition comprising the combination of a finely divided montmorillonite mineral sufficiently modified with quaternary ammonium cations containing 10 or more carbon atoms, per cation, to render the mineral compatible with the oil, a polar organic dispersing agent for the mineral, and a partial ester of a fatty acid of 10 to 20 carbon atoms and a saturated, aliphatic, polyhydric alcohol having 3 to 18 hydroxyl groups, at least 2 of said hydroxyl groups being unesterified. In a preferred embodiment, useful, for example, in preparing an emulsion of an aqueous solution of aluminum chlorohydrate in cyclomethicone, the emulsifying composition is the combination of (a) a gelatinous dispersion of stearalkonium hectorite, with propylene carbonate dispersing agent, in isopropyl myristate, and (b) polyglyceryl-4 oleate.

43 Claims, No Drawings

WATER-IN-OIL EMULSIONS

This invention relates to water-in-oil emulsions. More particularly, it is directed to an emulsifier combination which provides water-in-oil emulsions of improved stability which are especially suitable for being dispensed as nonflammable aerosols. The invention also concerns a method of preparing such emulsions.

Liquid compositions of all types are currently available in pressurized containers from which they can be dispensed in aerosol form. Antiperspirants, space deodorants, bactericides, insecticides, and hair sprays are but a few examples of these. Pressurization is usually provided by an inert, normally gaseous propellant being present in the container under superatmospheric pressure. The propellant is miscible with the liquid to be dispensed, and a dip tube in the container communicates the liquid contents with an aerosol dispensing valve at the top of the container. When the valve is opened the propellant forces itself and the liquid through the dip tube and out the valve, causing the liquid to be broken up into small, airborne particles.

It is generally desirable, for obvious reasons, that the emission from aerosol cans be nonflammable. This has led to the extensive use of chlorofluorocarbon propellants such as trichloromonofluoromethane and dichlorodifluoromethane, which are safe in that respect. Recent studies indicate, however, that chlorofluorocarbon gases, if they reach the earth's upper atmosphere, might react with ozone there and significantly reduce its concentration. Since ozone screens out most of the ultraviolet irradiation that is beamed from the sun to the earth, it is feared that a decreased ozone concentration in the earth's upper atmosphere may have various ill effects, such as an increase in the risk and incidence of skin cancer in humans. For this reason there is a need to develop effective aerosol compositions which use other types of propellants.

Normally gaseous hydrocarbons such as propane, n-butane, and isobutane can be used as aerosol propellants, but their extreme flammability generally requires that they be mixed with a flame retardant, such as water. Hydrocarbon propellants are immiscible in water however; so in order to obtain a truly effective, aerosol dispensible composition with those ingredients, it is desirable to emulsify one in the other. While oil-in-water emulsions can be used for some applications, there are reasons to prefer the water-in-oil emulsions, also called oil-out emulsions, for most emulsion type aerosols. For one thing, the volume of hydrocarbon in the container will often substantially exceed that of the aqueous phase, so that a complete oil-in-water emulsion might be difficult or impossible to achieve. Secondly, where the liquid composition is a personal care product aerosol droplets which have a surface coating of an oleaginous material—produced by water-in-oil emulsions—feel less wet when they strike the skin, which enhances consumer acceptance.

To be completely suitable for aerosol dispensing, a water-in-oil emulsion must, among other things, be stable for relatively long periods of time, and if separation does occur it must not cause a hard layer of solids to settle on the bottom of the container. We have found that such an emulsion can be achieved by use of an emulsifying composition comprised of the combination of (a) a finely divided montmorillonite mineral sufficiently modified with quaternary ammonium cations containing 10 or more carbon atoms, per cation, to render the mineral compatible with the oleaginous liquid, (b) a polar organic dispersing agent for the mineral, and (c) a partial ester of a fatty acid of 10 to 20 carbon atoms and a saturated, aliphatic, polyhydric alcohol having 3 to 18 hydroxyl groups, at least 2 of the hydroxyl groups being unesterified.

Montmorillonite minerals are the main component of bentonite clays and include montmorillonite itself, beidellite, nontronite, hectorite, saponite, and sauconite. Most preferred for use in the present invention is hectorite, sometimes called magnesium bentonite, a fluorine containing, hydrous silicate associated with magnesium, lithium, and sodium cations.

The montmorillonite mineral used in the present invention must first be rendered organophilic by the exchange of some or all of its surface-positioned metallic cations for quaternary ammonium cations. The organic radicals in the quaternary ammonium cations provide at least 10, preferably 25 to 40, carbon atoms per ion. Hydrocarbon radicals are preferred, such as aliphatic hydrocarbyl groups (e.g., alkyl) and aralkyl hydrocarbyl groups (e.g., phenylalkyl). Preferably each quaternary ammonium ion will have at least one aliphatic hydrocarbyl group of 16 to 18 carbon atoms, e.g. n-octadecyl or n-hexadecyl. Most preferred are stearalkonium cations, i.e., stearyldimethylbenzyl ammonium ions.

Preparation of organically modified montmorillonite minerals to be used in the practice of the present invention can be by known methods, for example as described in U.S. Pat. No. 2,531,427 to Hauser and U.S. Pat. No. 2,966,506 to Jordan. Basically, their preparation involves treatment of an aqueous slurry of the mineral in finely divided form with a sodium ion exchange resin to replace the other metal cations with sodium ions, followed by mixing of the treated clay slurry with a quaternary ammonium chloride compound to replace the sodium ions with quaternary ammonium ions.

The second component of the emulsifying combination used in the present invention, the polar organic dispersing agent, ensures the dispersion of the organophilic montmorillonite mineral in the oleaginous liquid. It is advantageously present in an amount of about 2 to 6 parts per each 100 parts by weight of the mineral, and is preferably an oxygen containing compound of 4 to 7 carbon atoms, e.g., an alcohol, ketone, ether, carbonate, or carbonyl ester. Most preferred are the alkylene carbonates.

The third component of the emulsifying combination used in practicing the present invention, i.e., the partial ester of the aliphatic polyhydric alcohol, is employed in an amount effective to emulsify the water, usually about 0.3 to 4.4 parts per each 100 parts by weight of the emulsion. Preferred fatty acid moieties in the partial ester are those of 16 to 18 carbon atoms, preferably those which are saturated or monoethylenically unsaturated, e.g., oleic and isostearic moieties.

The polyhydric alcohol used to prepare the partial ester emulsifier preferably has at least 4 hydroxyl groups, and the ester itself preferably has at least 3 unesterified hydroxy groups. The carbon atom content of the alcohol is preferably within the range of 6 to 24, e.g., 9 to 18. Alkyl alcohols such as pentaerythritol and sorbitol can be used, as can ether alcohols such as polyglycerols, e.g., polyglycerols having 3 to 6 glycerol units.

The water-in-oil emulsions of the present invention can be prepared with any of a variety of oleaginous liquids, including silicon oils such as dimethylsiloxanes; fatty acid esters such as monohydric, lower alkyl alcohol esters of saturated fatty acids of 12 to 18 carbon atoms; mineral spirits; and hydrocarbon oils, such as dodecane, iso-tetradecane, and the isomeric decanes. Usually the oleaginous liquid will constitute about 5 to 70 weight percent of the emulsion.

The present invention can be practiced not only in the formulation of liquid aerosol compositions, but in the preparation of water-in-oil emulsions in general. The emulsifying composition is generally harmless and nonirritating to human skin, which renders the invention especially useful in the preparation of liquid medicaments and personal care products.

Depending on their intended use, the emulsions of the present invention can range in viscosity from water thin liquids, e.g., for aerosol antiperspirants or space deodorants, to heavy, viscous fluids, e.g., as in skin treatment creams.

The emulsions of the present invention may contain components other than the water and the oleaginous liquid which would be considered the active ingredients, and those components may be either hydrophilic or organophilic.

In antiperspirant compositions, for instance, there may be present as the principal active ingredient a perspiration inhibitor such as aluminum chlorohydrate, zinc chloride, aluminum glycine complexes, or aluminum chlorohydrate allantoin complexes. Also useful in antiperspirant and body deodorant compositions are bactericides such as 1-(3-chloro-allyl)-3,5,7-triaza-1-azoniaadamantane chloride (quaternium-15), 5-chloro-2-(2,4-dichlorophenoxy) phenol (triclosan), and formalin.

Emollients such as isopropyl myristate, isopropyl palmitate, and myristyl propionate can be included in emulsions that are to be applied to the skin, as can humectants such as glycerol and polyglycols and anti-irritants such as glycine and certain mixed aliphatic esters known in the art.

Preparation of the water-in-oil emulsions of the present invention can be accomplished in a variety of ways, but we have found one method to be greatly preferred, which is as follows:

The water is heated to a temperature in the range of about 120 to 150 degrees F., for example in an agitated, jacketted stainless steel tank. In a separate vessel the oleaginous liquid is also heated to a temperature in the range of about 120 to 150 degrees F. Into the heated oleaginous liquid is added and dissolved (i) the partial ester of the fatty acid and (ii) a gelatinous dispersion in an organic vehicle of the organically modified montmorillonite mineral, together with the polar organic dispersing agent. Finally, the heated water is added to the heated oleaginous solution, while agitating the mixture to form a highly stable water-in-oil emulsion.

Using a pre-formed gel of the organophilic montmorillonite mineral to prepare the emulsion compositions of the present invention greatly facilitates the process. Preparation of the gel can be by mixing together the mont-morillonite mineral, the organic vehicle, and the polar organic dispersing agent using high shear mixing equipment, such as an homogenizer or suitable shear pump.

The organic vehicle for forming the mineral gel can be any of a large variety of organic liquids, for example the same compounds as comprise the oleaginous component of the emulsion, such as mineral oil, petroleum spirits, or fatty acid esters, e.g., glycerides and monohydric and dihydric, lower alkyl alcohol esters of fatty acids of 6 to 20 carbon atoms. As specific examples of suitable vehicles for forming such a gel may be mentioned castor oil, isopropyl myristate, lanolin oil, isopropyl palmitate, propylene glycol dicaprylate, and propylene glycol dicaproate. Preferably, the pre-formed gel will contain about 2 to 15 weight percent of the organically-modified montmorillonite mineral. A preferred pre-formed gel is one containing about 5 to 15 weight percent stearalkonium hectorite, 80 to 90 weight percent isopropyl myristate, and about 2 to 5 weight percent propylene carbonate. Preferably, about 15 to 50 parts by weight of such a dispersion will be used per each 100 parts by weight of the oleaginous liquid.

In preparing self propellant antiperspirant compositions of the present invention, it is preferred that cyclomethicones, which are cyclic dimethyl polysiloxanes of about 3 to 6 siloxane units, be used as the oleaginous liquid, advantageously in combination with isopropyl myristate, which can serve also as an emollient and as the organic vehicle for a pre-formed gel of the montmorillonite mineral. When used in such a composition, it is generally advantageous to employ a weight ratio of cyclomethicone to total isopropyl myristate within the range of about ½ to 3/1. Excluding the isopropyl myristate contained in the pre-formed montmorillonite gel, if any, an advantageous ratio of cyclomethicone to isopropyl myristate is about 3/1 to 5/1.

A preferred partial ester for the emulsifying composition of the present invention is polyglyceryl-4 oleate, which is an ester of oleic acid and a glycerol polymer containing an average of 4 glycerol units. Preferably, it is used in a ratio of about 2.5 to 20 parts, per each 100 parts by weight of the water.

The preferred organic vehicle for the pre-formed montmorillonite gel is isopropyl myristate, and the preferred montmorillonite mineral is stearalkonium hectorite. When those two are used in combination, it is generally preferred to employ in the pre-formed gel a weight ratio of stearalkonium hectorite to isopropyl myristate within the range of about 1/5 to 1/15.

Water-in-oil emulsions prepared in accordance with the present invention are highly stable and can be safely and effectively dispensed in aerosol form when combined in a pressurized container with a normally gaseous propellant. Where one or more hydrocarbons are used as the propellant, it is preferred that the emulsion contain sufficient water to render the self propellant composition nonflammable. In this regard, by "nonflammability" is meant the ability to pass the Flame Propagation Test recited in the Federal Hazardous Substances Act, Part 191.15(a) and (b). To achieve such nonflammability it is generally preferred to add about 150 to 350 parts by weight of the water to each 100 parts by weight of the oleaginous solution.

Aerosol packaging of the water-in-oil emulsions of the present invention can be by known methods. A preferred propellant for antiperspirant use is a mixture of isobutane and propane, for example in a weight ratio of about 1 to 10 parts isobutane per part of propane.

A preferred antiperspirant composition of the present invention is an emulsion comprised of water, about 25 to 50 parts cyclomethicone per each 100 parts by weight of the water, about 4 to 20 parts isopropyl myristate per each 10 parts of the cyclomethicone, about 20 to 80 parts aluminum chlorohydrate per each 100 parts by weight of the water, about 5 to 15 parts polyglyceryl-4 oleate per each 100 parts by weight of the water, about 0.5 to 3 parts stearalkonium hectorite per each 100 parts by weight of the water, and about 2 to 4 parts propylene carbonate per each 10 parts by weight of the stearalkonium hectorite. For aerosol dispensing it is preferred to mix 100 parts by weight of this composition with about 105 to 130 parts of a mixture of isobutane and propane containing a weight ratio of isobutane to propane within the range of about 1/1 to 2/1.

The following examples will illustrate some specific embodiments of the invention.

EXAMPLE 1

This example illustrates the preparation and aerosol packaging of a liquid antiperspirant composition of the present invention.

The formulation for the composition is as follows:

| Ingredient | Parts by Weight |
| --- | --- |
| Aluminum Chlorohydrate (50 wt. % aqueous solution) | 20.00 |
| Deionized Water | 10.10 |
| Cis-1-(3-chloroallyl)-3,5,7-triaza-1-azoniaadamantane Chloride | 0.10 |
| Polyglyceryl-4 Oleate | 1.50 |
| Gelatinous Mixture of Stearalkonium Hectorite (10 wt. %), Isopropyl Myristate (86.7 wt. %) and Propylene Carbonate (3.3 wt. %) | 2.50 |
| Isopropyl Myristate | 1.50 |
| Cyclomethicone | 7.05 |
| Perfume Oil | 0.25 |
| Mixture of Isobutane (59 wt. %) and Propane (41 wt. %) | 57.00 |

The method of combining the above ingredients is as follows:

Into a first mixing tank is introduced the aluminum chlorohydrate, the deionized water, and the cis-1-(3-chloroallyl)-3,5,7-triaza-1-azoniaadamantane chloride. The ingredients are blended together and heated to 135–145 degrees F.

Into a second mixing tank is introduced the isopropyl myristate and the cyclomethicone, which are also blended together and heated to 135–145 degrees F. To the silicone oil mixture of the second tank are then added, with stirring and maintenance of temperature, the polyglyceryl-4 oleate and the gelatinous mixture of stearalkonium hectorite, isopropyl myristate, and propylene carbonate. Stirring is continued until the gel is completely dissolved and for 10 minutes thereafter, following which the silicone oil solution is filtered through a 150 mesh (Tyler) screen and a 50 micron filter canister.

The aqueous mixture of the first tank is filtered through a 50 micron filter canister and added, with gentle stirring and maintenance of temperature, to the silicone oil solution to form a water-in-oil emulsion. After the addition is complete, heating is stopped and stirring is continued until the emulsion temperature drops to 100 degrees F. At this point the perfume oil is blended into the composition.

Typically the final product may be packaged by adding the emulsion to size 202×314 aerosol cans in an amount of 50.9 grams per can, and then crimping the cans closed and fitting them with vertical action spray valves of the following specification:

Stem: Nylon, 0.013 inch orifice
Housing: Nylon, 0.013 inch orifice
Dip tube: Polyethylene, 0.122 inch i.d.

The mixture of isobutane and propane may then be pumped into the emulsion-containing cans in the amount of 67.4 grams per can. The resulting package has excellent shelf life, is nonflammable, and produces a uniform fine spray of commercially acceptable antiperspirant composition. The pressure within the can is approximately 75 psig. at 70 degrees F.

EXAMPLE 2

This example illustrates the preparation of an aerosol personal deodorant composition of the present invention.

The formulation for the composition is as follows:

| Ingredient | Parts by Weight |
| --- | --- |
| Deionized Water | 30.00 |
| Mixture of Sorbitan Sesquioleate (98.5 wt. %) and Polyglyceryl-4 Oleate (1.5%) | 1.00 |
| Gelatinous Mixture of Stearalkonium Hectorite (10 wt. %), Isopropyl Myristate (86.7%) and Propylene Carbonate (3.3%) | 2.00 |
| Cyclomethicone | 7.00 |
| AP fluid | 1.00 |
| Triclosan | 0.20 |
| Perfume Oil | 0.20 |
| Mixture of Isobutane (84 wt. %) and Propane (16%) | 58.80 |

The above ingredients are combined and packaged in the same manner as described in Example 1, except that the aqueous phase consists only of the water. The amount of the ingredients placed in each can is adequate to provide an internal pressure at 70 degrees F. of about 50 psig.

EXAMPLE 3

This example illustrates the preparation and aerosol packaging of an athlete's foot remedial composition of the present invention.

The formulation for the composition is as follows:

| Ingredient | Parts by Weight |
| --- | --- |
| Talc | 4.00 |
| Tolnaftate | 0.10 |
| Cyclomethicone | 3.00 |
| S.D. Alcohol No. 40-1 (200 degrees) | 3.00 |
| De-ionized Water | 10.00 |
| Gelatinous mixture of Stearalkonium Hectorite (10.0 wt. %), Isopropyl myristate (86.7 wt. %) and Propylene Carbonate (3.3 wt. %) | 6.00 |
| Polyglycerol-4 Oleate | 0.10 |
| Oleyl Diethanolamide | 0.90 |
| Mixture of Isobutane (90 wt. %) and Propane (10 wt. %) | 72.92 |

The above ingredients are combined and packaged in the following manner:

The tolnaftate, cyclomethicone, stearalkonium hectorite gel and the surfactants are blended together and warmed to about 135 degrees F., following which the blend is filtered. The alcohol and water are mixed together, warmed to 130 degrees F., and then added to the oil phase. The resulting emulsion is placed into cans, to which is then added the talc. Lastly, the cans are pressurized with the isobutane/propane mixture.

EXAMPLE 4

This example illustrates the preparation and aerosol packaging of a liquid space deodorant composition of the present invention.

The formulation for the composition is as follows:

| Ingredient | Parts by Weight |
| --- | --- |
| Deionized Water | 30.00 |
| Gelatinous Mixture of Stearalkonium Hectorite (10 wt. %), Isopropyl Stearate (86.7 wt. %) and Propylene Carbonate (3.3 wt. %) | 2.00 |
| Sorbitan Sesquioleate | 1.00 |
| Cyclomethicone | 7.00 |
| AP Fluid | 1.00 |
| Triclosan | 0.20 |
| Perfume Oil | 0.20 |
| Mixture of Isobutane (84 wt. %) and Propane (16 wt. %) | 58.60 |

The above ingredients are combined and packaged in the following manner:

The deionized water is heated to 120 degrees F. The remaining ingredients, except the propellant mixture, are blended together, filtered, and heated to 130 degrees F. Using good agitation, the water is added to the oil phase.

The resulting emulsion is added to aerosol cans, which are then pressure filled with the propellant blend. The final pressure is preferably about 50 psig. at 70 degrees F., depending upon the efficiency of the vacuum crimping operation as a means of reducing the partial pressure of air in the can.

EXAMPLE 5

This example illustrates the preparation and aerosol packaging of an insecticide composition of the present invention.

The formulation for the composition is as follows:

| Ingredient | Parts by Weight |
| --- | --- |
| Pyrethrum Intermediate Blend MGK 5192 | 5.56 |
| Odorless Mineral Spirits | 5.44 |
| Polyglyceryl-4 Oleate | 1.00 |
| Gelatinous Mixture of Stearalkonium Hectorite (10 wt. %), Isopropyl Myristate (86.7 wt. %) and Propylene Carbonate (3.3 wt. %) | 7.00 |
| De-ionized Water | 31.00 |
| Mixture of Isobutane (60 wt. %) and Propane (40 wt. %) | 50.00 |

The above ingredients are combined and packaged in the following manner:

The first four ingredients are combined and warmed to about 125 degrees F. The water is also warmed to 125 degrees F.

The water is added to the oil-phase with adequate agitation to form a water-in-oil emulsion.

The emulsion is poured into suitable aerosol cans, which are then pressure loaded with the propellant blend to a pressure of about 65 psig. at 70 degrees F.

EXAMPLE 6

This example illustrates the preparation and aerosol packaging of a silicone lubricant of the present invention.

The formulation for the composition is as follows:

| Ingredient | Parts by Weight |
| --- | --- |
| Silicone Fluid (50 cps.) | 2.0 |
| Odorless Mineral Spirits | 22.0 |
| Polyglycerol-4 Oleate | 1.5 |
| Gelatinous Mixture of Stearalkonium Hectorite (10 wt. %), N.F. Mineral Oil (86.7 wt. %) and Propylene Carbonate (3.3 wt. %) | 2.5 |
| De-ionized Water | 62.0 |
| Mixture of Isobutane (84 wt. %) and Propane (16 wt. %) | 10.0 |

The above ingredients are combined and packaged in the following manner:

The first four items are combined, filtered, and warmed to 120–130 degrees F., following which the de-ionized water is added slowly and with good agitation to form a creamy emulsion. The emulsion is placed in cans, which are then charged with the propellant mixture.

EXAMPLE 7

This example illustrates the preparation and aerosol packaging of a grit-containing cleanser for hard surfaces.

The formulation for the composition is as follows:

| Ingredient | Parts by Weight |
| --- | --- |
| Odorless Mineral Spirits | 13.0 |
| Polyglyceryl-4 Oleate | 5.0 |
| Gelatinous Mixture of Stearalkonium Hectorite (10.0 wt. %), N.F. Mineral Oil (86.7 wt. %) and Propylene Carbonate (3.3 wt. %) | 7.0 |
| Methyl Pyrrolidone | 3.0 |
| Finely Ground Silica | 5.0 |
| De-ionized Water | 27.0 |
| Mixture of Isobutane (60 wt. %) and Propane (40 wt. %) | 40.0 |

The above ingredients are combined and packaged in the following manner:

The first four items are blended, warmed to 130 degrees F. and filtered.

The water is warmed to 130 degrees F. and added slowly to the oil-phase with good agitation to form an oil-out emulsion.

After the oil-out emulsion has cooled to 100–110 degrees F. the silicon powder is added slowly, with good agitation, following which the mixture is poured into aerosol cans and the cans are charged with the hydrocarbon propellant mixture.

It is claimed:

1. In a water-in-oil emulsion containing water, an oleaginous liquid, and an emulsifying composition, the improvement wherein the emulsifying composition is comprised of the combination of a finely divided montmorillonite mineral sufficiently modified with quaternary ammonium cations containing 10 or more carbon atoms, per cation, to render the mineral compatible with the oleaginous liquid, a polar organic dispersing agent for the mineral, and a partial ester of a fatty acid of 10 to 20 carbon atoms and a saturated, aliphatic, polyhydric alcohol having 3 to 18 hydroxyl groups, at least 2 of said hydroxyl groups being unesterified.

2. The water-in-oil emulsion of claim 1, wherein the montmorillonite mineral is hectorite.

3. The emulsion of claim 2, wherein the polyhydric alcohol has at least 4 hydroxyl groups and at least 3 of said hydroxyl groups are unesterified.

4. The emulsion of claim 3, wherein the quaternary ammonium ions contain at least 1 aliphatic hydrocarbon radical of 16 to 18 carbon atoms, per ion.

5. The emulsion of claim 1, wherein the montmorillonite mineral is stearalkonium hectorite.

6. The emulsion of claim 1, wherein the fatty acid contains 16 to 18 carbon atoms and the polyhydric alcohol is a polyglycerol of 3 to 6 glycerol units.

7. The emulsion of claim 6, wherein the fatty acid is oleic acid.

8. The emulsion of claim 1, wherein the partial ester is polyglyceryl-4 oleate.

9. The emulsion of claim 1, wherein the polar organic dispersing agent is an alkylene carbonate.

10. The emulsion of claim 1, wherein the polar organic dispersing agent is propylene carbonate.

11. The emulsion of claim 1, wherein the oleaginous liquid comprises a silicone oil.

12. The emulsion of claim 11, wherein the oleaginous liquid additionally comprises a monohydric, lower alkyl alcohol ester of a saturated fatty acid of 12 to 18 carbon atoms.

13. The emulsion of claim 1, wherein the oleaginous liquid comprises cyclomethicone and isopropyl myristate.

14. A liquid, self propellant composition comprising, under superatmospheric pressure, (a) a water-in-oil emulsion of water, oleaginous liquid, and an emulsifying composition comprised of the combination of a finely divided montmorillonite mineral sufficiently modified with quaternary ammonium cations containing 10 or more carbon atoms, per cation, to render the mineral compatible with the oleaginous liquid, a polar organic dispersing agent for the mineral, and a partial ester of a fatty acid of 10 to 20 carbon atoms and a saturated, aliphatic, polyhydric alcohol having 3 to 18 hydroxyl groups, at least 2 of said hydroxyl groups being unesterified; (b) liquid phase, normally gaseous propellant; and (c) vapor phase, normally gaseous propellant.

15. The composition of claim 14, wherein the liquid phase propellant and the vapor phase propellant consist essentially of one or more hydrocarbons, and the water-in-oil emulsion contains sufficient water to render the composition nonflammable.

16. The composition of claim 15 wherein the water-in-oil emulsion contains a perspiration inhibitor.

17. The composition of claim 16, wherein the perspiration inhibitor is aluminum chlorohydrate.

18. The composition of claim 16, wherein the oleaginous liquid comprises a silicone oil and a monohydric, lower alkyl alcohol ester of a saturated fatty acid of 12 to 18 carbon atoms.

19. The composition of claim 16, wherein the oleaginous liquid is comprised of cyclomethicone and isopropyl myristate.

20. The composition of claim 19, wherein the montmorillonite mineral is hectorite.

21. The composition of claim 19, wherein the modified montmorillonite mineral is stearalkonium hectorite.

22. The composition of claim 21, wherein the fatty acid contains 16 to 18 carbon atoms and the polyhydric alcohol is a polyglycerol of 3 to 6 glycerol units.

23. The composition of claim 21, wherein the fatty acid is oleic acid.

24. The composition of claim 21, wherein the partial ester is polyglyceryl-4 oleate.

25. The composition of claim 21, wherein the polar organic dispersing agent is alkylene carbonate.

26. The composition of claim 21, wherein the polar organic dispersing agent is propylene carbonate.

27. A liquid, self propellant, antiperspirant composition comprising (a) a water-in-oil emulsion of water, cyclomethicone, isopropyl myristate, aluminum chlorohydrate, and an emulsifying composition comprised of the combination of finely divided stearalkonium hectorite, propylene carbonate, and polyglyceryl-4 oleate, and (b) a mixture of isobutane and propane, said composition being under sufficient pressure to cause a portion of the mixture of isobutane and propane to be in the liquid state.

28. The composition of claim 27, wherein the cyclomethicone is present in an amount of about 25 to 50 parts per each 100 parts by weight of the water, the stearalkonium hectorite is present in an amount of about 0.5 to 3 parts per each 100 parts by weight of the water, the propylene carbonate is present in an amount of about 2 to 4 parts per each 10 parts by weight of the stearalkonium hectorite, the polyglyceryl-4 oleate is present in an amount of about 5 to 15 parts per each 100 parts by weight of the water, the isopropyl myristate is present in an amount of about 4 to 20 parts per each 10 parts by weight of the cyclomethicone, and the mixture of isobutane and propane is present in an amount of about 105 to 130 parts per each 100 parts by weight of the emulsion.

29. A process of preparing a highly stable emulsion of water in an oleaginous liquid, comprising the steps of (a) heating the water to a temperature in the range of about 120 to 150 degrees F., (b) heating the oleaginous liquid to a temperature in the range of about 120 to 150 degrees F., (c) dissolving in the heated oleaginous liquid (i) a partial ester of a fatty acid of 10 to 20 carbon atoms and a saturated, aliphatic, polyhydric alcohol having 3 to 18 hydroxyl groups, at least 2 of said hydroxyl groups being unesterified, and (ii) a gelatinous dispersion in an organic vehicle of a finely divided montmorillonite mineral sufficiently modified with quaternary ammonium cations containing 10 or more carbon atoms, per cation, to render the mineral compatible with the oleaginous liquid, said dispersion containing a polar organic dispersing agent for the mineral, and (d) adding the heated water to the heated oleaginous solution while agitating the mixture to form a highly stable water-in-oil emulsion.

30. The process of claim 29, wherein the montmorillonite mineral is hectorite.

31. The process of claim 30, wherein the polyhydric alcohol has at least 4 hydroxyl groups and at least 3 of said hydroxyl groups are unesterified.

32. The process of claim 31, wherein the quaternary ammonium ions contain at least 1 aliphatic hydrocarbon radical of 16 to 18 carbon atoms, per ion.

33. The process of claim 28, wherein the montmorillonite mineral is stearalkonium hectorite.

34. The process of claim 28, wherein the fatty acid contains 16 to 18 carbon atoms and the polyhydric alcohol is a polyglycerol of 3 to 6 glycerol units.

35. The process of claim 34, wherein the fatty acid is oleic acid.

36. The process of claim 28, wherein the partial ester is polyglyceryl-4 oleate.

37. The process of claim 28, wherein the polar organic dispersing agent is an alkylene carbonate.

38. The process of claim 28, wherein the polar organic dispersing agent is propylene carbonate.

39. The process of claim 28, wherein the oleaginous liquid comprises a silicone oil.

40. The process of claim 39, wherein the oleaginous liquid additionally comprises a monohydric, lower alkyl alcohol ester of a saturated fatty acid of 12 to 18 carbon atoms.

41. The process of claim 28, wherein, in step (a), a perspiration inhibitor is dissolved in the water.

42. The process of claim 41, wherein the perspiration inhibitor is aluminum chlorohydrate.

43. The process of claim 42, wherein the oleaginous liquid comprises cyclomethicone and isopropyl myristate.

* * * * *